United States Patent [19]

Kisida et al.

[11] Patent Number: 4,987,145
[45] Date of Patent: Jan. 22, 1991

[54] ACARICIDAL OR INSECTICIDAL SUBSTITUTED 1-PHENYLALKYL BENZIMIDAZOLE COMPOUNDS

[75] Inventors: Hirosi Kisida, Takarazuka; Akira Shuto, Takarazuka; Masahiro Tamaki, Takarazuka; Tomotoshi Imahase, Takarazuka; Hiroaki Fujimoto, Toyonaka, all of Japan

[73] Assignee: Sumitomo Chemical Company, Limited, Osaka, Japan

[21] Appl. No.: 395,057

[22] Filed: Aug. 17, 1989

[30] Foreign Application Priority Data

Sep. 9, 1988 [JP] Japan .................................. 63-226792

[51] Int. Cl.$^5$ ..................... A01N 43/52; C07D 235/08
[52] U.S. Cl. ..................................... 514/394; 548/325
[58] Field of Search ......................... 548/325; 514/394

[56] References Cited

U.S. PATENT DOCUMENTS 4,612,323  9/1986  Kisida et al. .................. 514/394
4,663,339  5/1987  Kisida et al. .................. 514/394

OTHER PUBLICATIONS

"Insecticidal Benzimidazoles with a Terpenoid Moiety", Eiichi Kuwano et al., Department of Agricultural Chemistry, Kyushu University, Mar. 3, 1982, pp. 1715–1716.

Chemical Abstracts, vol. 102, No. 19, Abstract 166,754y, p. 621, May 13, 1985.

Primary Examiner—Mary C. Lee
Assistant Examiner—Zinna Northington Davis
Attorney, Agent, or Firm—Birch, Stewart, Kolasch & Birch

[57] ABSTRACT

A benzimidazole compound of the formula:

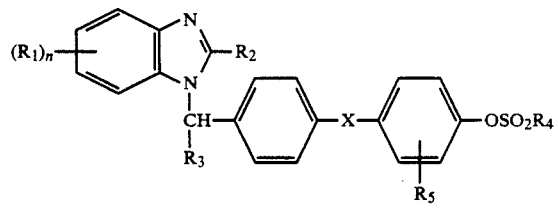

wherein $R_1$ is a hydrogen atom, a halogen atom, a lower alkyl group, a lower alkoxy group or a lower alkylthio group, $R_2$ is a hydrogen atom, a lower alkyl group or a halo(lower)-alkyl group, $R_3$ is a hydrogen atom or a lower alkyl group, $R_4$ is a lower alkyl group or a halo(lower)alkyl group, $R_5$ is a hydrogen atom, a halogen atom or a lower alkyl group, X is an oxygen atom, a methylene group, an imino group or a group of the formula: $-S(O)_m-$ in which m is an integer of 0 to 2 and n is an integer of 1 to 4, which is useful as an insecticide and/or acaricide.

20 Claims, No Drawings

ACARICIDAL OR INSECTICIDAL SUBSTITUTED 1-PHENYLALKYL BENZIMIDAZOLE COMPOUNDS

The present invention relates to benzimidazole derivatives, and their production and use. More particularly, it relates to benzimidazole compounds (hereinafter referred to as "benzimidazole(s)") of the formula:

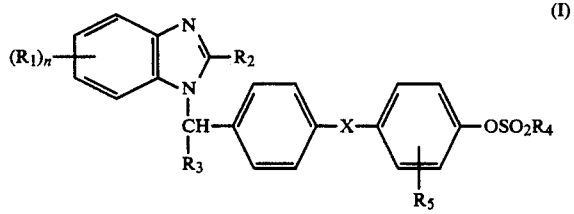

wherein $R_1$ is a hydrogen atom, a halogen atom, a lower alkyl group, a lower alkoxy group or a lower alkylthio group, $R_2$ is a hydrogen atom, a lower alkyl group or a halo(lower)alkyl group, $R_3$ is a hydrogen atom or a lower alkyl group, $R_4$ is a lower alkyl group or a halo(lower)alkyl group, $R_5$ is a hydrogen atom, a halogen atom or a lower alkyl group, X is an oxygen atom, a methylene group, an imino group or a group of the formula: $-S(O)_m-$ in which m is an integer of 0 to 2 and n is an integer of 1 to 4, and their production and use as insecticides and/or acaricides.

The term "lower" as hereinabove and hereinafter used is intended to mean usually a group having not more than 8 carbon atoms, preferably not more than 5 carbon atoms. Specifically, $R_1$ may be hydrogen, fluorine, chlorine, bromine, iodine, methyl, ethyl, n-propyl, isopropyl, isobutyl, sec-butyl, methoxy, ethoxy, n-propoxy, isopropoxy, methylthio, ethylthio, n-propylthio, isopropylthio or the like. Specific examples of $R_2$ are hydrogen, methyl, ethyl, isopropyl, trifluoromethyl, difluoromethyl, etc. Specific examples of $R_3$ are hydrogen, methyl, ethyl, etc. $R_4$ may represent, for instance, methyl or trifluoromethyl. $R_5$ can be, for instance, hydrogen, fluorine, chlorine or methyl.

It is known that some kinds of benzimidazole derivatives show an insecticidal and/or acaricidal activity (Agric.Biol. Chem., 46 (6) 1715 (1982); U.S. Pat. Nos. 4,612,323 and 4,663,339). However, their insecticidal and/or acaricidal effect is not necessarily sufficient.

It has now been found that the benzimidazoles (I) exert an excellent insecticidal activity against harmful insects belonging to Lepidoptera (e.g. diamondback, cabbage armyworm), Hemiptera (e.g. brown rice planthopper, green rice leafhopper), Diptera (e.g. common mosquito), Coleoptera (e.g. corn root worm), Dyctioptera (e.g. German cockroach), etc. It has also been found that they show a prominent acaricidal activity against acarids which belong to Acarina (e.g. two-spotted spider mite, carmine spider mite, Kanzawa spider mite, citrus red mite, European red mite). Advantageously, their insecticidal and/or acaricidal activity is effective for the insects and acarids having resistance to conventional insecticides and/or acaricides. The benzimidazoles (I) are thus useful as the active ingredients for agricultural or sanitary insecticides and/or acaricides.

The benzimidazoles (I) of the invention can be produced by various procedures, of which typical examples are shown below:

Procedure A

The benzimidazole (I) is obtainable by subjecting an anilide of the formula:

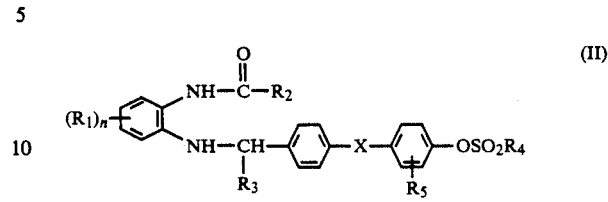

wherein $R_1$, $R_2$, $R_3$, $R_4$, $R_5$, X and n are each as defined above to ring closure in the presence of an acid catalyst.

The reaction for ring closure is usually carried out in an inert solvent such as benzene, toluene, xylene, o-dichlorobenzene, chloroform or carbon tetrachloride. A carboxylic acid of the formula:

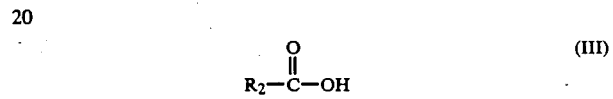

in which $R_2$ is as defined above and corresponds to the one in the anilide (II) used as the starting material is also usable as the solvent. In this case, the carboxylic acid (III) can serve as the acid catalyst, too. Examples of the acid catalyst other than the carboxylic acid are sulfuric acid, p-toluenesulfonic acid, benzenesulfonic acid, etc. Normally, the reaction temperature is from room temperature to the boiling temperature of the reaction mixture, and the reaction time is from about 0.5 to about 50 hours. Removal of the by-produced water from the reaction system is effective in promotion of the reaction.

After completion of the reaction, the reaction mixture is subjected to post-treatment by a per se conventional procedure. When desired, the product may be purified by a per se conventional procedure such as chromatography, distillation or recrystallization.

Procedure B

The benzimidazole (I) is obtainable by reacting an aniline of the formula:

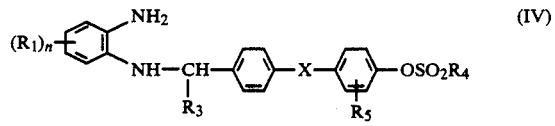

wherein $R_1$, $R_3$, $R_4$, $R_5$, X and n are each as defined above with the carboxylic acid (III) or its reactive derivative.

As the reactive derivative of the carboxylic acid (III), there are exemplified acid anhyarides, ortho-acid esters, acid halides, acid esters, etc. The reaction is usually carried out in the presence or absence of an inert solvent such as water, benzene, toluene, carbon tetrachloride, chloroform or ethylene chloride at a temperature of about 25° to about 200° C., preferably about 50° C. to the boiling temperature of the reaction mixture for a period of about 1 to about 50 hours. The molar ratio of the aniline (IV) and the carboxylic acid (III) or its reactive derivative may be about 1:1–100, preferably about 1:1–10.

The reaction mixture is subjected to post-treatment by a per se conventional procedure. When desired, the product may be purified by a per se conventional procedure such as column chromatography, distillation or recrystallization.

Procedure C

The benzimidazole (I) is obtainable by reacting a benzimidazole of the formula:

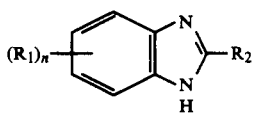

wherein $R_1$, $R_2$ and n are each as defined above with a benzyl compound of the formula:

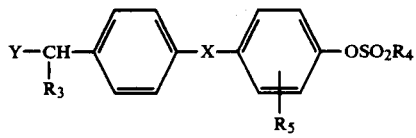

wherein $R_3$, $R_4$, $R_5$ and X are each as defined above and Y is a leaving group (e.g. halogen, tosyloxy, mesyloxy) in the presence of an acid binding agent.

The reaction is carried out in the presence of an acid binding agent, usually in an inert solvent at a temperature of about $-30°$ C. to the boiling temperature of the reaction mixture, preferably about 0° to about 110° C., for a period of about 0.5 to about 50 hours. Examples of the acid binding agent are alkali metals (e.g. lithium, sodium, potassium), alkali metal hydrides (e.g. sodium hydride, potassium hydride), alkali metal amides (e.g. sodium amide), alkali metal hydroxides (e.g. sodium hydroxide, potassium hydroxide), alkali metal carbonates (e.g. sodium carbonate, potassium carbonate), organic bases (e.g. triethylamine, N,N-dimethylaniline, N,N-diethylaniline), etc. Examples of the solvent are water, hydrocarbons (e.g. benzene, toluene, xylene), ethers (e.g. diethyl ether, diisopropyl ether, dioxane, tetrahydrofuran, ethylene glycol dimethyl ether, dimethoxyethane), ketones (e.g. acetone, methylethylketone, methylisobutylketone, cyclohexanone), acid amides (e.g. dimethylformamide, diethylformamide, dimethylacetamide), sulfoxides (e.g. dimethylsulfoxide), etc. In order to accelerate the reaction, a phase transfer catalyst such as benzyltriethylammonium chloride or tetrabutylammonium bromide may be employed. The molar ratio of the benzimidazole (V) and the benzyl compound (VI) is usually about 1:0.1–10, preferably 1:0.8–1.0. Also, the molar ratio of the benzimidazole (V) and the acid binding agent is normally about 1:0.9–1.1.

The reaction mixture may be subjected to post-treatment by a per se conventional procedure. When desired, the product may be purified by a per se conventional procedure such as column chromatography, distillation or recrystallization.

The anilide (II) and the aniline (IV) are novel and can be produced by a per se conventional procedure. For instance, they may be produced according to the scheme as shown below:

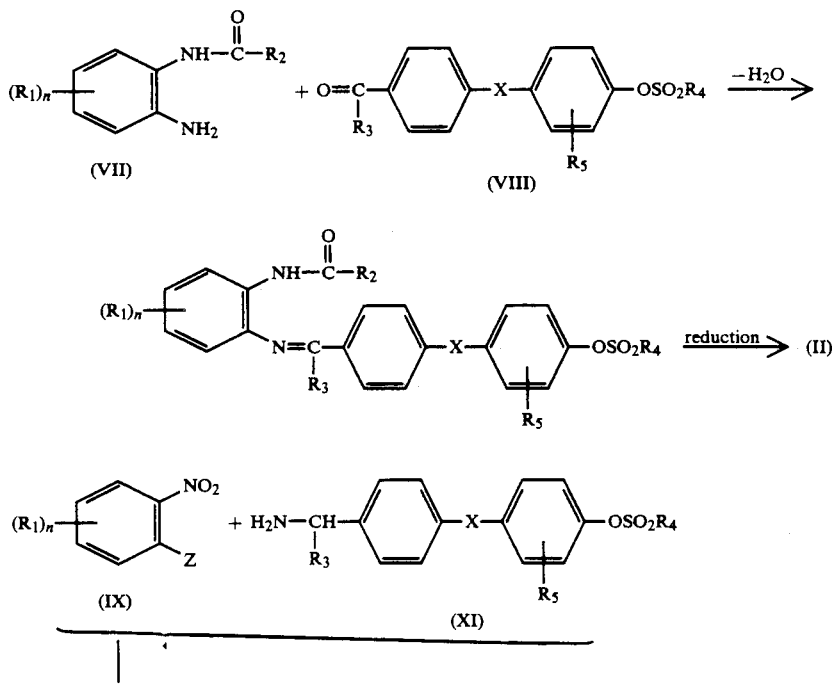

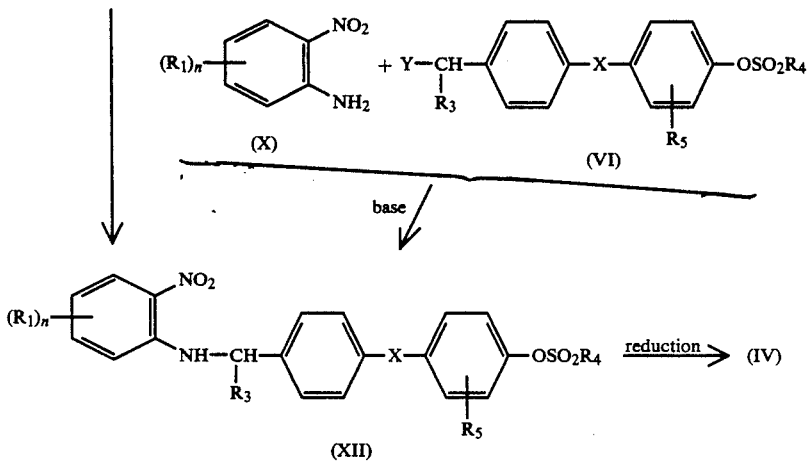

wherein $R_1$, R , $R_3$, $R_4$, $R_5$, X, Y and n are each as defined above and Z is a halogen atom.

Practical and presently preferred embodiments for preparation of the benzimidazole (I) are illustratively shown in the following Production Examples.

Production Example 1

A mixture of 2-acetylamino-N-[4-(4-trifluoromethylsulfonyloxyphenoxy)benzyl]aniline (500 mg), p-toluenesulfonic acid (50 mg) and toluene (50 ml) was heated under reflux while removing the by-produced water therefrom through a Dean-Stark trap. After the by-production of water ceased, the reaction mixture was cooled to room temperature, washed with a saturated sodium carbonate solution and water in order and distilled under reduced pressure to eliminate toluene. The residue was purified by silica gel column chromatography to give 2-methyl-1-[4-(4-trifluoromethylsulfonyloxyphenoxy)benzyl]benzimidazole (433 mg) as a colorless oil. $n_D^{25.0}$1.5670.

Production Example 2

A mixture of 2-fluoro-6-[4-(4-methylsulfonyloxyphenoxy)benzylamino]aniline (300 mg) and ethyl orthoacetate (181 mg) was heated at 150° to 160° C. for 24 hours while stirring. The reaction mixture was cooled to room temperature, toluene (100 ml) and a 5% sodium hydroxide solution (50 ml) were added thereto, and the resultant mixture was stirred for 10 minutes The toluene layer was separated, washed with water, dried over anhydrous sodium sulfate and distilled under reduced pressure to eliminate toluene. The residue was purified by silica gel column chromatography to give 4-fluoro-1-[4-(4-methylsulfonyloxyphenoxy)benzyl]-2-methylbenzimidazole (243 mg) as white crystals m.p., 48°-56° C.

Production Example 3

A mixture of 2-chloro-6-[4-(4-trifluoromethylsulfonyloxyphenoxy)benzylamino]aniline (300 mg) and acetic acid (5 ml) was heated under reflux for 6 hours. The reaction mixture was cooled to room temperature, excessive acetic acid was removed by distillation under reduced pressure, and toluene (100 ml) and a 5% sodium hydroxide solution (50 ml) were added thereto, followed by stirring for 10 minutes. The toluene layer was separated, washed with water, dried over anhydrous sodium sulfate and distilled under reduced pressure to eliminate toluene The residue was purified by silica gel column chromatography to give 4-chloro-2-methyl-1-[4-(4-trifluoromethylsulfonyloxyphenoxy)benzyl]benzimidazole (285 mg) as a colorless liquid. $n_D^{24}$1.5655.

Production Example 4

To a mixture of anhydrous N,N-dimethylformamide (10 ml) and sodium hydride (60% oil suspension; 29 mg), 4-fluoro-2-methylbenzimidazole (110 mg) was added while stirring, and stirring was continued at room temperature for 1 hour. To the reaction mixture, a solution of 4-(4-trifluoromethylsulfonyloxyphenoxy)benzyl bromide (300 mg) in anhydrous N,N-dimethylformaide (3 ml) was dropwise added, followed by stirring at room temperature for 5 hours. After completion of the reaction, the reaction mixture was poured into water (100 ml) and extracted with toluene (30 ml) two times. The toluene extract was washed with water, dried over anhydrous sodium sulfate and distilled under reduced pressure to eliminate toluene The residue was purified by silica gel column chromatography to give 4-fluoro-2-methyl-1-[4-(4-trifluoromethylsulfonyloxyphenoxy)benzyl]benzimidazole (164 mg) as a colorless liquid $n_D^{26}$1.5615.

From the second fraction, there was obtained 7-fluoro-2-methyl-1-[4-(4-trifluoromethylsulfonyloxyphenoxy)benzyl]benzimidazole (135 mg) as a colorless liquid. $n_D^{26}$1.5515.

In the same manner as above, the benzimidazoles (I) as shown in Table 1 were obtained.

TABLE 1

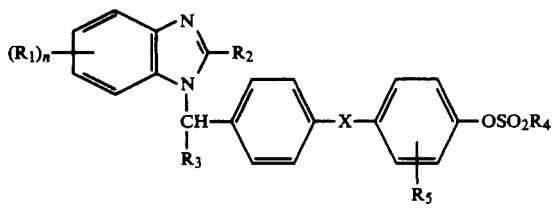

| Compound No. | $(R_1)_n$ | $R_2$ | $R_3$ | $R_4$ | $R_5$ | X | Physical constant |
|---|---|---|---|---|---|---|---|
| 1 | H | $CH_3$ | H | $CF_3$ | H | O | $n_D^{25}$ 1.5670 |
| 2 | 4-Cl | $CH_3$ | H | $CF_3$ | H | O | $n_D^{24}$ 1.5655 |
| 3 | 4-Cl | H | H | $CF_3$ | H | O | $n_D^{24.5}$ 1.5667 |
| 4 | 4-Cl | $CH_3$ | $CH_3$ | $CF_3$ | H | O | $n_D^{25}$ 1.5651 |
| 5 | 7-F | $CH_3$ | H | $CF_3$ | H | O | $n_D^{26}$ 1.5515 |
| 6 | 4-iso-$C_3H_7$ | $CH_3$ | H | $CF_3$ | H | O | $n_D^{24.9}$ 1.5427 |
| 7 | 5-F | $CH_3$ | H | $CF_3$ | H | O | $n_D^{25.1}$ 1.5518 |
| 8 | 6-F | $CH_3$ | H | $CF_3$ | H | O | $n_D^{27.0}$ 1.5525 |
| 9 | 4,7-$F_2$ | $CH_3$ | H | $CF_3$ | H | O | $n_D^{24}$ 1.5502 |
| 10 | H | $CF_3$ | H | $CF_3$ | H | O | $n_D^{25}$ 1.5456 |
| 11 | 4-F | $CH_3$ | H | $CH_3$ | H | O | m.p., 48–56° C. |
| 12 | 4-$CH_3$ | $CH_3$ | H | $CF_3$ | H | O | $n_D^{24.5}$ 1.5596 |
| 13 | 4-Cl | $CH_3$ | H | $CF_3$ | H | S | $n_D^{25.2}$ 1.6165 |
| 14 | 4-Cl | $CH_3$ | H | $CF_3$ | H | $CH_2$ | $n_D^{25}$ 1.5790 |
| 15 | 4-Cl | $CH_3$ | H | $CF_3$ | H | $SO_2$ | $n_D^{24.2}$ 1.6174 |
| 16 | 4-Cl | $CH_3$ | H | $CF_3$ | H | SO | $n_D^{25}$ 1.6209 |
| 17 | 4-Cl | $CH_3$ | H | $CF_3$ | H | NH | $n_D^{26.4}$ 1.5750 |
| 18 | 4-Cl | $CH_3$ | H | $CF_3$ | 2-$CH_3$ | O | $n_D^{24.1}$ 1.5457 |
| 19 | 4-Cl | $CH_3$ | H | $CF_3$ | 3,5-$(CH_3)_2$ | O | $n_D^{24.0}$ 1.5398 |
| 20 | 4-Cl | $CH_3$ | $CH_3$ | $CF_3$ | 2-Cl | O | $n_D^{24.5}$ 1.5465 |
| 21 | 4-F | $CH_3$ | H | $CF_3$ | H | O | $n_D^{26}$ 1.5615 |
| 22 | 4-$OC_2H_5$ | $CH_3$ | H | $CF_3$ | H | O | $n_D^{24.4}$ 1.5705 |
| 23 | 4-$SCH_3$ | $CH_3$ | H | $CF_3$ | H | O | $n_D^{26}$ 1.6216 |
| 24 | 4-Br | $CH_3$ | H | $CF_3$ | H | O | $n_D^{26}$ 1.5926 |
| 25 | 4-Cl | $C_2H_5$ | H | $CF_3$ | H | O | $n_D^{24}$ 1.5604 |
| 26 | 4-Cl | iso-$C_3H_7$ | H | $CF_3$ | H | O | $n_D^{24.1}$ 1.5549 |
| 27 | 4-$OCF_2CF_2H$ | $CH_3$ | H | $CF_3$ | H | O | $n_D^{25.5}$ 1.5672 |

On the application of the benzimidazole (I) as an insecticidal and/or acaricidal composition, it may be used as such or in an appropriate preparation form such as oil sprays, emulsifiable concentrates, wettable powders, flowables, granules, dusts, aerosols, fumigants (e.g. mosquito coil, electric mosquito mat, low temperature fumigant), non-heating fumigants (e.g. self-combustible fumigant, chemically reactive fumigant), non-heating vaporizing agents or toxic baits. In those preparations, the benzimidazole (I) is usually contained in an amount of about 0.01 to about 95% by weight.

Said preparation can be formulated in a per se conventional manner by mixing at least one of the benzimidazole (I) with an appropriate solid, liquid or gaseous carrier(s) or diluent(s). An appropriate adjuvant(s) such as a surfactant, an adherent, a dispersant or a stabilizer may be also mixed therein for improving the dispersibility and other properties of the preparation.

Examples of the solid carriers or diluents are clays (e.g. kaolin clay, diatomaceous earth, synthetic hydrated silica, bentonite, fubasami clay, terra alba), talcs, ceramics, other inorganic minerals (e.g. sericite, quartz, sulfur, active carbon, calcium carbonate, hydrated silica), chemical fertilizers (e.g. ammonium sulfate, ammonium phosphate, ammonium nitrate, urea, ammonium chloride), etc. Examples of the liquid carriers or diluents are alcohols (e.g. methanol, ethanol), ketones (e.g. acetone, methylethylketone), aromatic hydrocarbons (e.g. benzene, toluene, xylene, ethylbenzene, methylnaphthalene), aliphatic hydrocarbons (e.g. hexane, kerosene, lamp oil), alcyclic hydrocarbons (e.g. cyclohexane), esters (e.g. ethyl acetate, butyl acetate), nitriles (e.g. acetonitrile, isobutyronitrile), ethers (e.g. diisopropyl ether, dioxane), acid amides (e.g. N,N-dimethylformamide, N,N-dimethylacetamide), halogenated hydrocarbons (e.g. dichloromethane, trichloroethane, carbon tetrachloride), dimethylsulfoxide, botanical oils (e.g. soybean oil, cotton-seed oil), etc. Examples of the gaseous carriers or diluents are Freon gas, butane gas, LPG (liquefied petroleum gas), dimethyl ether, carbon dioxide, etc.

The surfactants usable for emulsification, dispersion or spreading may be any of ionic and non-ionic types. Their examples are alkylsulfates, alkylarylsulfonates, dialkylsulfosuccinate, polyoxyethylene alkylaryl ether, phosphates of polyoxyethylene alkylaryl ethers, condensates of naphthalenesulfonic acid and formalin, etc. Examples of the non-ionic surfactants are polyoxyethylene alklyl ethers, polyoxyethylene polyoxypropylene blocked copolymers, sorbitan fatty acid esters, polyoxyethylene sorbitan fatty acid esters, etc. Examples of the adherents or dispersants may include casein, gelatin, polyvalent alcohols (e.g. starch powder, gum arabic, cellulose derivatives, alginic acid), lignin derivatives, bentonite, saccharides, synthetic aqueous high molecular compounds (e.g. polyvinyl alcohol, polyvinylpyrrolidone, polyacrylic acid), etc. As the stabilizers, there may be used alkyl phosphates (e.g. PAP (isopropyl acid phosphate), BHT (2,6-di-t-butyl-4-methyl-phenol), BHA (mixture of 2-t-butyl-4-methoxyphenol and 3-t-butyl-4-methoxyphenol), botanical oils, mineral oils, surfactants, aliphatic acids or esters, etc.

As the base or carrier for mosquito coil, there are used vegetable powders (e.g. wooden powders, lees) in combination with a binding agent (e.g. powders of *Machilus thunbergii*, starch, gluten). The base for electric mosquito mat is a hardened plate of fibrils comprising cotton linter, optionally admixed with pulp. The base for self-combustible fumigant comprises an exothermic burning agent (e.g. nitrate, nitrite, guanidine salt, potassium chlorate, nitrocellulose, ethyl cellulose, wooden powders), a thermal decomposition initiator (e.g. alkaline earth metal salts, alkali metal salts, bichromates, chromates), an oxygen supplier (e.g. potassium nitrate), a burning support (e.g. melamine, wheat starch), an additive (e.g. diatomaceous earth), a binding agent (e.g. synthetic starch), etc. The base for chemically reactive fumigant comprises an exothermic agent (e.g. alkali metal sulfides, alkali metal polysulfides, alkali metal hydrosulfides, calcium oxide), a catalytic agent (e.g. carbonaceous material, iron carbide, activated clay), a organic foaming agent (e.g. azodicarbonamide, benzenesulfonylhydrazide, dinitrosopentamethylenetetramine, polystyrene, polyurethane), a filler (e.g. natural fibers, synthetic fibers), etc. As the base for non-heating vaporizing agent, there may be used thermoplastic resins, filter papers, Japanese papers, etc. The base for toxic baits may comprise food (e.g. grain powders, essential oils, sugar, crystalline cellulose), an antioxidant (e.g. dibutylhydroxytoluene, nordihydroguaiaretic acid), a preservative (e.g. dehydroacetic acid), a misfeed inhibitor (e.g. red pepper powders), a flavoring agent (e.g. cheese flavor, onion flavor), etc.

The benzimidazole (I) of the invention formulated into an appropriate preparation may be applied as such or in a form of dilution with water. In addition, said composition may contain other insecticides, nematicides, acaricides, soil vermin controlling agents, vermin controlling agents, fungicides, herbicides, plant growth regulators, synergistic agents, fertilizers, soil improvers, etc.

The dosage of the benzimidazole (I) as the active ingredient in an agricultural insecticidal and/or acaricidal composition is generally from about 0.5 to 500 grams per 10 are. When the composition is applied as emulsifiable concentrates, wettable powders or flowables, it is diluted with water usually to make a concentration of the active ingredient of about 1 to about 1000 ppm before the application. In case of such formulation as dusts, granules, etc., the composition may be applied as such without diluting with water. As a sanitary or household insecticidal and/or acaricidal composition, the application is usually made in the form of emulsifiable concentrates, wettable powders or flowables after dilution with water to make a concentration of the active ingredient of about 1 to about 1000 ppm. In case of oil sprays, aerosols, fumigants, toxic baits or the like, it may be applied as such. In any event, the practical dosage is much influenced by the sort of formulation, the application stage, the application place, the application procedure, the kind of insects or acarids, the extent of damage, etc. and therefore may be appropriately decided taking these conditions into consideration.

Some practical embodiments of the composition for the control of insects and/or acarids according to the invention are illustratively shown in the following Formulation Examples wherein % and part(s) are by weight and the compound numbers correspond to those in Table 1.

Formulation Example 1

One of Compound Nos. 1 to 27 (0.2 part), xylene (2 parts) and kerosene (97.8 parts) are well mixed to make an oil spray.

Formulation Example 2

One of Compound Nos. 1 to 27 (10 parts), polyoxyethylene styrylphenyl ether (14 parts), calcium dodecylbenzenesulfonate (6 parts), xylene (35 parts) and dimethylformamide (35 parts) are well mixed to make an emulsifiable concentrate.

Formulation Example 3

One of Compound Nos. 1 to 27 (20 parts), fenitrothion (O,O-dimethyl-O-(3-methyl-4-nitrophenyl)phosphorothioate) (10 parts), calcium ligninsulfonate (3 parts), sodium laurylsulfate (2 parts) and synthetic hydrated silica (65 parts) are well mixed in a pulverizer to make a wettable powder.

Formulation Example 4

One of Compound Nos. 1 to 27 (3 part), kaolin clay (87 parts) and talc (10 parts) are well mixed in a pulverizer to make dusts.

Formulation Example 5

One of Compound Nos. 1 to 27 (20 parts), sodium naphthalenesulfonate-formalin condensate (3 parts) and water (75 parts) are mixed well, and methyl cellulose (2 parts) as an adherent is added thereto to make a flowable.

Formulation Example 6

One of Compound Nos. 1 to 27 (5 parts), synthetic hydrated silica (1 part), calcium ligninsulfonate (2 parts), bentonite (30 parts) and kaolin clay (62 parts) are well mixed in a pulverizer. The resultant mixture is kneaded well with water and granulated by the aid of a granulator, followed by drying to give granules.

Formulation Example 7

One of Compound Nos 1 to 27 (0.05 part), tetramethrin (N-(3,4,5,6-tetrahydrophthalimido)methyl chrysanthemate) (0.2 part), resmethrin (5-benzyl-3-furylmethyl (±)-cis,trans-chrysanthemate) (0.05 part), xylene (7 parts) and deodorized lamp oil (42.7 parts) are well mixed and charged into an aerosol container. Upon attachment of a valve portion, a pressurizing agent (LPG) (50 parts) is charged through the valve to make an aerosol.

Formulation Example 8

One of Compound Nos. 1 to 27 (0.3 g) is added to d-trans-allethrin ((±)-3-allyl-2-methyl-4-oxo-2-cyclopentenyl d-trans-chrysanthemate) (0.3 g) in methanol (20 ml). The resultant mixture is combined with base material for mosquito coil (powdes of *Machilus thunbergii*: lees: wooden powders=3:5:1) (99.4 g) and uniformly mixed. After evaporation of methanol, the resulting mixture is admixed with water (150 ml), molded and dried to make a mosquito coil.

The following Test Examples present some typical test data indicating the excellent insecticidal and/or acaridal activities of the benzimidazoles (I). The compounds used for comparison are shown in Table 2:

TABLE 2

| Compound symbol | Structure | Remarks |
|---|---|---|
| A | (benzimidazole with N-CH2-CH=C(CH3)-CH2-CH2-CH=C(CH3)-CH3 side chain) | Abric.Biol. Chem., 46 (6), 1715 (1982) |
| B | Cl-C6H3(CH3)-N=CH-N(CH3)2 | Chlordimeform (N'-(4-chloro-2-methylphenyl)-N,N-dimethylformamidine) |
| C | (4-Cl-C6H4)2C(OH)(CCl3) | Dicofol (1,1-bis(chlorophenyl)-2,2,2-trichloroethanol) |
| D | 2-methylbenzimidazole-1-CH2-C6H4-O-C6H4-OC2H5 | U.S. Pat. No. 4,612,323; Compound No. 50 |
| E | 4-chloro-2-methylbenzimidazole-1-CH2-C6H4-O-C6H4-OC2H5 | U.S. Pat. No. 4,663,339; Compound No. 7 |
| F | (cyclohexyl)3-SnOH | Plictran ® (tricyclohexyltin hydroxide) |

Test Example 1

Adults of female carmine spider mites (*Tetranychus cinnabarinus*) were permitted to live on leaves (10 mites per leaf) of kidney bean seven days after sowing in the pots, and the mites were kept at 25° C. in a greenhouse. After 6 days, a 200 fold dilution (ca. 500 ppm) of the emulsifiable concentrate prepared according to Formulation Example 2 was sprayed over the pots placed on a turn table at a spray volume of 10 ml per pot, and also 2 ml of the dilution were applied to the soil in each pot. Eight days thereafter, the plant damage by the mites was observed with two replications and evaluated according to the following criteria:

—: no material damage to leaves
+: slight damage to leaves
++: same damage as seen in untreated plot The results are shown in Table 3.

TABLE 3

| Test compound | Plant damage |
|---|---|
| 1 | — |
| 2 | — |
| 3 | — |
| 4 | — |
| 5 | — |
| 6 | — |
| 7 | — |
| 8 | — |
| 9 | — |
| 10 | — |
| 11 | — |
| 12 | — |
| 13 | — |
| 14 | — |
| 15 | — |
| 16 | — |
| 17 | — |
| 18 | — |
| 19 | — |
| 20 | — |
| 21 | — |
| 22 | — |
| 23 | — |
| 24 | — |
| 25 | — |
| 26 | — |
| 27 | — |
| A | ++ |
| B | + |
| C | −+ |

Test Example 2

All stages of two-spotted spider mites (*Tetranychus urticae*) were permitted to live on leaves of kidney bean grown in two pots, and the emulsifiable concentrate prepared according to Formulation Example 2 was sprayed over the pots in the designated concentration as shown in Table 4 at a spray volume of 20 ml per pot. Separately, 2 ml of said dilution were applied to the soil in each pot. The number of female adult was counted before and after the treatment (4, 8 and 18 days thereafter). The results are shown in Table 4.

TABLE 4

| Test compound | Concentration (ppm) | Number of female adult/2 pots | | | |
|---|---|---|---|---|---|
| | | Before treatment | 4 Days after treatment | 8 Days after treatment | 18 Days after treatment |
| 2 | 50 | 81 | 0 | 0 | 0 |
| D | 100 | 110 | 10 | 6 | 15 |
| E | 100 | 132 | 11 | 2 | 10 |
| F | 100 | 47 | 31 | 10 | 126 |
| Untreated | — | 77 | 131 | 132 | 314 |

Test Example 3

An emulsifiable concentrate prepared according to Formulation Example 2 was diluted with water to make a concentration of 10 ppm. The dilution (100 ml) was charged in a plastic cup (each 180 ml volume), and twenty last instar larvae of common mosquito (*Culex pipiens pallens*) were released therein. The larvae were bred until emergence, and the rate of emergence inhibition was observed with two replications.

The rate of emergence inhibition was determined according to the following criteria:
Rate of emergence inhibition
  a: more than 90% inhibition
  b: 90% to 80% inhibition
  c: less than 80% inhibition The results are shown in Table 5.

TABLE 5

| Test compound | Rate of emergence inhibition (%) |
|---|---|
| 2 | a |
| Untreated | c |

Test Example 4

Seven days after sowing, adults of diamondback moth (*Plutella xylostella*) were released to cotyledons of three radishes for oviposition (about 15 eggs per one cotyledon). The cotyledons were dipped in a 200 fold dilution (ca. 500 ppm) of the emulsifiable concentrate prepared according to Formulation Example 2 for 30 seconds. After air-drying, the seedlings were taken into a cup made of polyethylene at the bottom of which were placed a filter paper. Six days thereafter, survived larvae were observed with two replications to obtain a mortality (%). The results are shown in Table 6.

TABLE 6

| Test compound | Mortality (%) |
|---|---|
| 2 | 100 |
| Untreated | 5 |

Test Example 5

The emulsifiable concentrate prepared according to Formulation Example 2 was diluted with water to make a concentration of 500 ppm, and 2 ml of the dilution was applied onto 13 g of artificial diet for tobacco cutworm (*Spodoptera litura*), which was then taken into a cup made of polyethylene. Ten 4th-instar larvae of tobacco cutworm were released therein, and mortality (%) of the larvae was observed with two replications. The results are shown in Table 7.

TABLE 7

| Test compound | Mortality (%) |
|---|---|
| 2 | 100 |
| D | 5 |
| E | 5 |
| Untreated | 5 |

Test Example 6

Seedlings of rice plants (14 days after sowing) were dipped in a dilution (1000 ppm) of the emulsifiable concentrate prepared according to Formulation Example 2 for 1 minute. After air-drying, the stems were taken into a glass tube containing 1 ml of water. The 3rd-instar nymphs of brown rice planthopper (*Nilaparvata lugens*) were released therein and the glass tube was kept at 25° C. in a climate-conditioned box. Five days thereafter, mortality (%) was observed with two replications. The results are shown in Table 8.

TABLE 8

| Test compound | Mortality (%) |
|---|---|
| 2 | 100 |
| Untreated | 3 |

Test Example 7

The emulsifiable concentrate prepared according to Formulation Example 2 was diluted with water to make a concentration of 50 ppm, and the dilution (1 ml) was dropped in a filter paper placed at the bottom of a polyethylene cup (diameter, 5.5 cm). Twenty to thirty eggs of southern corn root worm and a grain of corn were taken therein. Eight days thereafter, survived larvae were observed with two replications to obtain a mortality (%). The results are shown in Table 9.

TABLE 9

| Test compound | Mortality (%) |
|---|---|
| 2 | 100 |
| Untreated | 5 |

What is claimed is:
1. A benzimidazole compound of the formula:

(TABLE 3-continued)

| Test compound | Plant damage |
|---|---|
| Untreated | ++ |

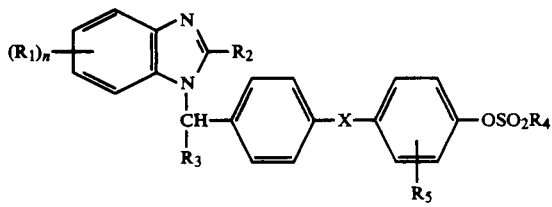

wherein $R_1$ is a hydrogen atom, a halogen atom, a lower alkyl group, a lower alkoxy group or a lower alkylthio group, $R_2$ is a hydrogen atom, a lower alkyl group or a halo(lower)alkyl group, $R_3$ is a hydrogen atom or a lower alkyl group, $R_4$ is a lower alkyl group or a halo(lower)alkyl group, $R_5$ is a hydrogen atom, a halogen atom or a lower alkyl group, X is an oxygen atom, a methylene group, an imino group or a group of the formula: —$S(O)_m$— in which m is an integer of 0 to 2 and n is an integer of 1 to 4.

2. The benzimidazole compound according to claim 1, wherein $R_2$ is a methyl group, $R_3$ is a hydrogen atom, $R_4$ is a halo(lower)alkyl group, $R_5$ is a hydrogen atom and X is an oxygen atom.

3. The benzimidazole compound according to claim 1, wherein $R_1$ is a chlorine atom at the 4-position, $R_2$ is a methyl group, $R_3$ is a hydrogen atom, $R_4$ is a trifluoromethyl group, $R_5$ is a hydrogen atom, X is an oxygen atom and n is 1.

4. The benzimidazole compound according to claim 1, wherein $R_1$ is a hydrogen atom, $R_2$ is a methyl group, $R_3$ is a hydrogen atom, $R_4$ is a trifluoromethyl group, $R_5$ is a hydrogen atom, X is an oxygen atom and n is 1.

5. An insecticidal or acaricidal composition which comprises as an active ingredient an insecticidally or acaricidally effective amount of the benzimidazole compound according to claim 1, and an inert carrier or diluent.

6. A method for controlling or exterminating insects or acarids which comprises applying as the active ingredient an insecticidally or acaricidally effective amount of the benzimidazole compound according to claim 1 to the locus where insects or acarids propagate.

7. The benzimidazole compound according to claim 1, wherein $R_1$ is hydrogen, fluorine, chlorine, bromine, iodine methyl, ethyl, n-propyl, isopropyl, isobutyl, sec-butyl, methoxy, ethoxy, n-propoxy, isopropoxy, methylthio, ethylthio, n-propylthio, or isopropylthio.

8. The benzimidazole compound according to claim 1, wherein $R_2$ is hydrogen, methyl, ethyl, isopropyl, trifluoromethyl or difluoromethyl.

9. The benzimidazole compound according to claim 1, wherein $R_3$ is hydrogen, methyl, or ethyl.

10. The benzimidazole compound according to claim 1, wherein $R_4$ is methyl or trifluoromethyl.

11. The benzimidazole compound according to claim 1, wherein $R_5$ is hydrogen, fluorine, chlorine or methyl.

12. The benzimidazole compound according to claim 1, wherein $R_1$ is hydrogen, fluorine, chlorine, bromine, iodine, methyl, ethyl, n-propyl, isopropyl, isobutyl, sec-butyl, methoxy. ethoxy, n-propoxy, isopropoxy, methylthio, ethylthio, n-propylthio, or isopropylthio; $R_2$ is hydrogen, methyl, ethyl, isopropyl, trifluoromethyl or difluoromethyl; $R_3$ is hydrogen, methyl, or ethyl; $R_4$ is methyl or trifluoromethyl; and $R_5$ is hydrogen, fluorine, chlorine or methyl.

13. The composition according to claim 5, wherein $R_2$ is a methyl group, $R_3$ is a hydrogen atom, $R_4$ is a halo(lower)alkyl group, $R_5$ is a hydrogen atom and X is an oxygen atom.

14. The composition according to claim 5, wherein $R_1$ is a chlorine atom at the 4-position, $R_2$ is a methyl group, $R_3$ is a hydrogen atom, $R_4$ is a trifluoromethyl group, $R_5$ is a hydrogen atom, X is an oxygen and n is 1.

15. The composition according to claim 5, wherein $R_1$ is a hydrogen atom, $R_2$ is a methyl group, $R_3$ is a hydrogen atom, $R_4$ is a trifluoromethyl group, $R_5$ is a hydrogen atom, X is an oxygen atom and n is 1.

16. The composition according to claim 5, wherein $R_1$ is hydrogen, fluorine, chlorine, bromine, iodine, methyl, ethyl, n-propyl, isopropyl, isobutyl, sec-butyl, methoxy, ethoxy, n-propoxy, isopropoxy, methylthio, ethylthio, n-propylthio, or isopropylthio; $R_2$ is hydrogen, methyl, ethyl, isopropyl, trifluoromethyl or difluoromethyl; $R_3$ is hydrogen, methyl, or ethyl; $R_4$ is methyl or trifluoromethyl, and $R_5$ is hydrogen, fluorine, chlorine or methyl.

17. The method according to claim 6, wherein $R_2$ is a methyl group, $R_3$ is a hydrogen atom, $R_4$ is a halo(lower)alkyl group, $R_5$ is a hydrogen atom and X is an oxygen atom.

18. The method according to claim 6, wherein $R_1$ is a chlorine atom at the 4-position, $R_2$ is a methyl group, $R_3$ is a hydrogen atom, $R_4$ is a trifluoromethyl group, $R_5$ is a hydrogen atom, X is an oxygen atom and n is 1.

19. The method according to claim 6, wherein $R_1$ is a hydrogen atom, $R_2$ is a methyl group, $R_3$ is a hydrogen atom, $R_4$ is a trifluoromethyl group, $R_5$ is a hydrogen atom, X is an oxygen atom and n is 1.

20. The method according to claim 6, wherein $R_1$ is hydrogen, fluorine, chlorine, bromine, iodine, methyl ,ethyl, n-propyl, isopropyl, isobutyl, sec-butyl, methoxy, ethoxy, n-propoxyl, isopropoxy, methylthio, ethylthio, n-propylthio, or isopropylthio; $R_2$ is hydrogen, methyl, ethyl, isopropyl, trifluoromethyl or difluoromethyl; $R_3$ is hydrogen, methyl, or ethyl; $R_4$ is methyl or trifluoromethyl; $R_5$ is hydrogen, fluorine, chlorine or methyl.

* * * * *